(12) United States Patent
Petrovic

(10) Patent No.: US 8,186,201 B2
(45) Date of Patent: May 29, 2012

(54) MULTI-SENSOR GAS DETECTORS

(75) Inventor: Dragan Petrovic, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 643 days.

(21) Appl. No.: 12/198,772

(22) Filed: Aug. 26, 2008

(65) Prior Publication Data

US 2010/0050744 A1    Mar. 4, 2010

(51) Int. Cl.
*G01N 25/00* (2006.01)
(52) U.S. Cl. ................................. 73/31.06; 73/25.01
(58) Field of Classification Search .......... 73/25.01, 73/31.06; 250/343
See application file for complete search history.

(56) References Cited

U.S. PATENT DOCUMENTS

| | | | | |
|---|---|---|---|---|
| 5,429,805 A | * | 7/1995 | Uno et al. | 422/83 |
| 5,721,430 A | * | 2/1998 | Wong | 250/339.13 |
| 6,469,303 B1 | * | 10/2002 | Sun et al. | 250/343 |
| 6,670,613 B2 | * | 12/2003 | Prozzo et al. | 250/345 |
| 7,502,109 B2 | * | 3/2009 | Bonne et al. | 356/328 |
| 2006/0060788 A1 | * | 3/2006 | Uchida et al. | 250/343 |
| 2006/0173637 A1 | * | 8/2006 | Martin | 702/24 |
| 2006/0180763 A1 | * | 8/2006 | Yoshida et al. | 250/343 |
| 2006/0262303 A1 | * | 11/2006 | Bonne et al. | 356/328 |
| 2007/0167853 A1 | * | 7/2007 | Melker et al. | 600/532 |
| 2008/0317087 A1 | * | 12/2008 | Kimura | 374/1 |

FOREIGN PATENT DOCUMENTS

EP          0 878 703 A3    2/1999

\* cited by examiner

*Primary Examiner* — John Fitzgerald
(74) *Attorney, Agent, or Firm* — Husch Blackwell LLP

(57) ABSTRACT

A multi-sensor gas detector includes a solid state heatable gas sensor, and at least one, different, infrared gas sensor. Emitted radiant energy from a heated surface of the solid state gas sensor, incident on the infrared gas sensor generates an output signal indicative thereof. The output signal and a signal from the solid state gas sensor can be coupled to evaluation circuits. The evaluation circuits can be implemented with a programmable processor and associated, executable control software to establish the presence of a target gas. One or more gas detectors can be incorporated into a regional monitoring system that includes a control unit coupled to a plurality of fire, smoke or gas detectors.

7 Claims, 1 Drawing Sheet

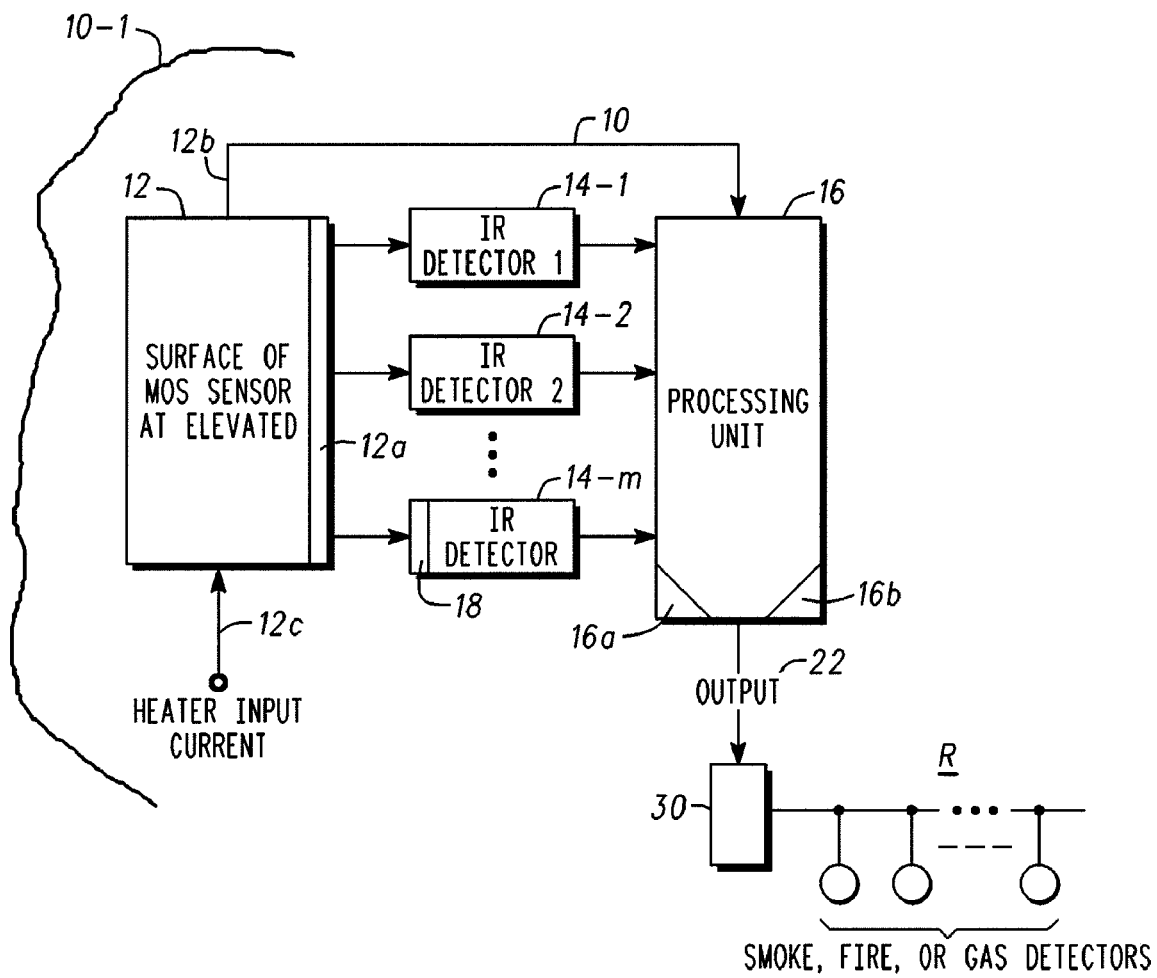

MULTI-SENSOR GAS DETECTORS

FIELD

The invention pertains to multi-sensor gas detectors. More particularly, the invention pertains to such detectors which include at least one solid state gas sensor and at least one non-dispersive infrared sensor.

BACKGROUND

Metal-Oxide-Semiconductor (MOS) chemical sensors require operation at elevated temperatures (typically between 200 C and 500 C). Another common feature of these sensors is lack of sufficient gas discrimination. In some applications (e.g. fire detection) it is acceptable if not desirable to detect presence of several gases. For instance Chromium Titanium Oxide (CTO) MOS sensor is sensitive to several gases commonly found in fires. Presence of any of those gases would generate signal that can be used to detect fire event. However, CTO's sensitivity to alcohols and few other molecular compounds that are commonly found in normal environment is so high that their presence obfuscates detection of desired target gases.

There are different ways of dealing with this issue. One approach is to prevent offending gases to reach sensor surface. Another is to add coatings such as chrome oxide or catalytic material that modify sensitivity to different gases. Combination of several MOS sensors with different coatings can be used as an "electronic nose" with appropriate signal analysis. However, in some applications (e.g. portable gas sensors) power consumption is critical parameter and combination of several sensors can not be implemented. Another approach is to take measurement at different temperature settings or take measurements as the temperature is increasing followed by signal analysis. Rationale of this approach is that MOS sensitivity to each gas is a strong function of temperature and it is conceivable that deconvolution of this data can recover information about type of gas detected by MOS sensor. Complexity of this approach along with the need to operate at higher temperature makes this approach very difficult.

There is thus a continuing need for lower power consuming multi-sensor gas detectors where combination of several sensors increases selectivity of the gas sensor. In complex applications like fire detection there is a number of gases that can be generated in different amounts. It is beneficial if sensor can detect any of those target gases. However, MOS sensors are sensitive to gases that are found in common environments. To improve performance of a detector one can add one or more sensors with a high degree of gas selectivity that can:

Positively identify presence of one specific target gas
Positively identify presence of one or more offending gases, or
Do both.

NDIR sensors have high degree of gas selectivity and although not perfect, can improve detection of events.

Another issue with MOS sensor is its accuracy. Its sensitivity to gases is highly dependent on temperature at its surface. For that reason it is desirable to be able to maintain desired temperature level at constant value.

BRIEF DESCRIPTION OF THE DRAWING

FIG. 1 is a block diagram of a detector in accordance with the invention.

DETAILED DESCRIPTION

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention combine at least one MOS sensor with a NDIR sensor to improve gas selectivity in an efficient manner. Sensing material of the MOS sensor is brought to an elevated temperature that is sufficiently high to generate substantial emission of electromagnetic radiation in mid-infrared part of the spectrum. Peak of the blackbody radiation follows Wien's displacement law. For instance, a black body kept at 450 C will have peak of its radiated electromagnetic spectrum at 4 microns. This is exactly the region of interest for identification of many gas molecules using NDIR (non-dispersive infrared) sensors.

Since MOS sensors are brought to elevated temperatures in operation, it would be preferred to use emitted radiation therefrom as an infrared source and conserve both power and space simultaneously. This embodiment will also eliminate some of the electronic circuitry at the same time.

In one aspect of the invention, gas selectivity is improved by simultaneously detecting one or more specific gases in combination with a signal generated by a MOS sensor. One or more IR detectors operate so as to sense the presence of a respective gas(es). The NDIR part of the combined sensor can target a desired gas(es) of interest, or offending gas(es) or both. In both cases an electronic processing unit can be provided with information that improves selectivity of this combined sensor. In another embodiment, additional gases of interest can be detected despite the fact that, in a given application, a particular MOS sensor is not sensitive to those gases. This may be useful if event to be detected may generate that particular gas that MOS sensor is not sensitive to.

In yet another aspect of the invention, one of the IR sensors can be used to improve accuracy of both MOS sensor and IR sensor(s). This can be achieved by providing one IR sensor with a broadband filter that passes IR light of all wavelengths. This signal can be used to control MOS sensor surface temperature accurately and simultaneously provide reference signal for NDIR measurements. NDIR detection schemes often use a reference detector that monitors overall light output from a light source. Noise that comes from the light source (in this case it is hot MOS sensor surface) can be filtered out in this manner.

Yet another aspect of the invention takes advantage of the fact that surface reactions are accompanied by emission of photons. When gas molecules adhere to the surface of a MOS sensor, the molecules either lose or gain electronic charge. This process also generates some light that is characteristic of that molecule. Half of the generated light is lost in the interior of the sensor. The rest of it escapes back into air.

In accordance with this aspect of the invention, light emitted by gas molecules during interaction with the surface of the MOS sensor can be detected. A suitable light sensor with an appropriate optical filter would help in identifying gases reacting with MOS sensor surface and assist in interpretation of MOS sensor signals.

FIG. 1 illustrates a multi-sensor 10 in accordance with the invention. Detector 10 can be carried by a housing 10-1. Detector 10 includes a metal oxide semiconductor (MOS)-type sensor 12 with an emitting surface 12a which can be heated by a heater input current 12c. Surface 12a when heated emits radiant, infrared energy sensed by a plurality of infrared sensors 14-1, -2 . . . -n. One or more of the sensors, such as 14-n can include a filter, such as filter 18, to limit the incident energy to a predetermined frequency band.

Each of the sensors 14-1, -2 . . . -n emits a respective output signal which can be coupled to a processing unit 16. An electrical output 12b of MOS sensor 12 can also be coupled to processing unit 16.

Processing unit 16, which could be implemented, at least in part, with a programmable computer 16a and executable control software 16b can evaluate inputs from the various sensors and determine if one or more target gases is present and generate an associated indicium 22. Indication or indicium 22 can be coupled to an alarm system 30 which monitors a region R for developing conditions such as the presence of selected gases, developing or actual fire condition.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas detector comprising:
   a solid state, heatable gas sensor having a heated surface wherein gas molecules of at least one target gas adhere to the heated surface and either gain or lose electronic charge thereby generating light that is characteristic of the at least one target gas during interaction with the heated surface of the solid state gas sensor;
   a plurality of infrared sensors of radiant energy, each of the plurality of infrared sensors oriented to receive light emitted from the heated surface of the solid state gas sensor;
   a filter that limits energy incident on at least one of the plurality of infrared sensors to a frequency band of the generated light that is characteristic of the molecules of the at least one target gas adhering to the surface; and
   control circuits responsive at least to outputs of the infrared sensors to establish the presence of the at least one target gas.

2. A detector as in claim 1 which includes a filter located adjacent to at least one of the infrared sensors.

3. A detector as in claim 2 where an output of the solid state gas sensor is coupled to the control circuits.

4. A detector as in claim 3 which includes electrical circuits to couple a heating current to the solid state gas sensor.

5. A detector as in claim 4 where the solid state gas sensor comprises a metal oxide semiconductor.

6. A detector as in claim 5 where the control circuits emit an indicium indicative of the established target gas.

7. A detector as in claim 6 where the control circuits include a programmable processor and associated executable control software prerecorded on a non-transitory computer readable medium.

\* \* \* \* \*